United States Patent
Kamimoto et al.

(10) Patent No.: US 9,315,473 B2
(45) Date of Patent: Apr. 19, 2016

(54) METHOD FOR PRODUCING PYROPHOSPHATE

(75) Inventors: Tetsuo Kamimoto, Saitama (JP); Takayoshi Kaneda, Saitama (JP); Hitoshi Kinoshita, Saitama (JP); Shinji Nakano, Saitama (JP); Susumu Ishii, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 13/821,641

(22) PCT Filed: Aug. 25, 2011

(86) PCT No.: PCT/JP2011/004726
§ 371 (c)(1),
(2), (4) Date: May 23, 2013

(87) PCT Pub. No.: WO2012/032728
PCT Pub. Date: Mar. 15, 2012

(65) Prior Publication Data
US 2013/0294994 A1    Nov. 7, 2013

(30) Foreign Application Priority Data

Sep. 9, 2010  (JP) ................................ 2010-202106

(51) Int. Cl.
*C01B 25/42*    (2006.01)
*C07D 251/56*  (2006.01)

(52) U.S. Cl.
CPC .............. *C07D 251/56* (2013.01); *C01B 25/42* (2013.01)

(58) Field of Classification Search
USPC ........................ 544/195; 423/305, 308, 311
See application file for complete search history.

(56) References Cited

U.S. PATENT DOCUMENTS

| 3,920,796 | A | * | 11/1975 | Sheridan ....................... 423/313 |
| 4,950,757 | A | | 8/1990 | Tomko et al. |
| 6,268,494 | B1 | | 7/2001 | Kasowski |
| 7,449,577 | B2 | | 11/2008 | Kimura et al. |
| 2006/0167256 | A1 | | 7/2006 | Kimura et al. |

FOREIGN PATENT DOCUMENTS

| EP | 0725065 A2 | 8/1996 |
| EP | 1674459 A1 | 6/2006 |
| JP | 2004 155764 A | 6/2004 |
| WO | 99/46250 A1 | 9/1999 |

OTHER PUBLICATIONS

International Search Report for PCT/JP2011/004726 dated Dec. 6, 2011.
Brodski, V. et al., "Structure of Melaminium Dihydrogenpyrophosphate and Its Formation from Melaminium Dihydrogenphosphate Studied with Powder Diffraction Data, Solid-State NMR, and Theoretical Calculations," J. Phys. Chem. B, 2004, vol. 108, pp. 15069-15076.
Feldman, W., "Melamine—Phosphoric Acid (1/2) C3H6N6 • 2H3PO4 and its Thermal Behavior," Z. Anorg. Allg. Chem., 1991, vol. 600, pp. 169-175, abstract only.
Volfkovic, V. S. I. et al., "Condensed Phosphate of Melamine," Z. anorg. allg. Chem., 1979, vol. 457, pp. 20-30, abstract only.
Tayama, I. et al., Phospahte no kagaku to Riyo, Kabushiki Kaisha Kagaku Kogyo Sha, Mar. 1, 1969, p. 141, formula 19.
English language Abstract of JP 2004 155764; dated Jun. 3, 2004; Shimonoseki Mitsui.
English Translation of EP0725065; dated Aug. 17, 1996.

* cited by examiner

*Primary Examiner* — Pancham Bakshi
(74) *Attorney, Agent, or Firm* — Millen, White, Zelano and Branigan, P.C.

(57) ABSTRACT

A producing method of a high-purity pyrophosphate comprising a calcination of the orthophosphate under the condition of 120° C.-350° C.; and a producing method suitable for manufacturing effectively the high-purity melamine pyrophosphate.

8 Claims, No Drawings

METHOD FOR PRODUCING PYROPHOSPHATE

TECHNICAL FIELD

The present invention relates to a producing method of pyrophosphate, and in particular to a producing method of melamine pyrophosphate useful as a flame retardant.

BACKGROUND ART

Pyrophosphate, especially melamine pyrophosphate is a compound obtained by binding pyrophosphoric acid, which is a condensed phosphoric acid, with melamine, and is a useful material as a flame retardant which is added to paint, synthetic resin or the like. Therefore, various kinds of methods for producing melamine pyrophosphate have been proposed.

For example, a producing method is disclosed wherein melamine is mixed with hydrochloric acid to make melamine hydrochloride salt in aqueous solution, then sodium pyrophosphate is added to precipitate the melamine pyrophosphate (Patent document 1). However, this method had a defect that a producing cost was high, since the expensive pyrophosphate should be used as a raw material, and a washing process by water and a filtration process were required in order to remove the halogen.

In addition, a producing method of melamine pyrophosphate is disclosed wherein pyrophosphoric acid is reacted with melamine at 0° C.-60° C. in aqueous solution (Patent document 2). However, in this case there was also a defect that producing cost was high, since expensive pyrophosphate should be used as a raw material, and a filtration process was required.

Furthermore, when pyrophosphate such as melamine pyrophosphate is manufactured by the dehydration condensation reaction, in some cases, not only pyrophosphate but also triphosphate and polyphosphate or the like are produced due to an overreaction. Therefore, there was a defect in this case that a degree of purity of pyrophosphate declines.

PRIOR ART DOCUMENTS

Patent Documents

Patent document 1: Japanese Patent Publication Tokkosyo 49-25675
Patent document 2: U.S. Pat. No. 4,950,757 Specification

SUMMARY OF THE INVENTION

The Problem to be Solved by the Invention

Therefore, the first object of the present invention is to provide an effective producing method for manufacturing a pyrophosphate with high-purity and high-yield.

The second object of the present invention is to provide an effective producing method for manufacturing a melamine pyrophosphate with high-purity and high-yield.

Means to Solve the Problem

As a result of intensive studies for attaining the aforementioned objects, the inventors of the present invention have found that the objects can be easily attained by a calcination of an orthophosphate, thereby achieving the present invention.

Namely, the present inventions are a producing method of a pyrophosphate comprising a calcination of the orthophosphate under a temperature condition of 120° C.-350° C., and a producing method of the melamine pyrophosphate comprising a calcination of the melamine orthophosphate under a temperature condition of 120° C.-350° C.

EFFECT OF THE INVENTION

According to the producing method of the present invention, the pyrophosphate having high purity can be efficiently provided, in particular, the melamine pyrophosphate having high purity can be efficiently provided for the reason that by-products such as melamine triphosphate and melamine polyphosphate due to overreaction are few.

EMBODIMENTS FOR CARRYING OUT THE INVENTION

Hereafter, the present invention will be described in more detail.

Examples of pyrophosphate which can be produced by the manufacturing method of the present invention are ammonium pyrophosphate, melamine pyrophosphate, acetoguanamine pyrophosphate, benzoguanamine pyrophosphate, acrylguanamine pyrophosphate, pyrophosphoric acid 2,4-diamino-6-nonyl-1,3,5-triazine, pyrophosphoric acid 2,4-diamino-6-hydroxy-1,3,5-triazine, pyrophosphoric acid 2-amino-4,6-dihydroxy-1,3,5-triazine, pyrophosphoric acid 2,4-diamino-6-methoxy-1,3,5-triazine, phyrophosphoric acid 2,4-diamino-6-ethoxy-1,3,5-triazine, pyrophosporic acid 2,4-diamino-6-propoxy-1,3,5-triazine, pyrophosphoric acid 2,4-diamino-6-isopropoxy-1,3,5-triazine, pyrophosphoric acid 2,4-diamino-6-mercapto-1,3,5-triazine and pyrophosphoric acid 2-amino-4,6-dimercapto-1,3,5-triazine.

More examples of pyrophosphate which can be produced by the manufacturing method of the present invention are pyrophosphoric acid N,N,N',N'-tetramethyl diaminomethane, pyrophosphoric acid ethylene diamine, pyrophosphoric acid N,N'-dimethyl ethylene diamine, pyrophosphoric acid N,N'-diethyl ethylene diamine, pyrophosphoric acid N,N-dimethyl ethylene diamine, pyrophosphoric acid N,N-diethyl ethylene diamine, pyrophosphoric acid N,N,N',N'-tetramethyl ethylene diamine, pyrophosphoric acid 1,2-propane diamine, pyrophosphoric acid 1,3-propane diamine, pyrophosophoric acid tetra methylene diamine, pyrophosphoric acid penta metylene diamine, pyrophosphoric acid hexa methylene diamine, pyrophosphoric acid 1,7-diamino heptane, pyrophosphoric acid 1,8-diamino octane, pyrophosphoric acid 1,9-diamino nonane, pyrophosphoric acid 1,10-diaminodecane, piperazine pyrophosphate, pyrophosphoric acid trans-2,5-dimethyl piperazine, pyrophosphoric acid 1,4-bis (2-aminoethyl)piperazine and pyrophosphoric acid 1,4-bis (3-aminopropyl)piperazine.

An example of particularly preferable pyrophosphate is melamine pyrophosphate for the reason that the pyrophosphate having high purity can be efficiently obtained.

An example of orthophosphate which is a raw material of the pyrophosphate used for the present invention is the orthophosphate which corresponds to the pyrophosphate cited previously. As for this orthophosphate, not only normal salt but also the acid salt as well as the mixture thereof may be used. In addition, corresponding base may be contained excessively.

The particularly preferable embodiment of the present invention is the producing method of melamine pyrophosphate using melamine orthophosphate as a raw material from the viewpoint that the pyrophosphate having high purity can be efficiently obtained. In this case, it is preferable that the melamine orthophosphate of a raw material is the orthophosphoric acidmelamine wherein 1 mol of melamine is bound with 1 mol of orthophosphoric acid.

The producing method of pyrophosphate of the present invention is a method for making pyrophosphate by carrying out a dehydration condensation reaction through a calcination of orthophosphate. In this case, it is preferable that the orthophosphate is calcined in the solid phase. Incidentally, even if a wet orthophosphate is used, the calcination is possible, or even if an aqueous slurry of the orthophosphate is used, the calcination is possible.

The calcination temperature of orthophosphate in the present invention should be 120° C.-350° C. From the viewpoints of purity and production efficiency of pyrophosphate obtained, 150° C.-300° C. is preferable and 160° C.-280° C. is more preferable.

If the calcination temperature is lower than 120° C., the reaction from orthophosphate to pyrophosphate does not progress sufficiently. If it is more than 350° C., triphosphate and other polyphosphate formed by further dehydration condensation reaction are produced, which is not preferable.

In addition, calcination time is not limited in particular. Until the dehydration condensation reaction from orthophosphate to pyrophosphate is completed, the calcination may be continued as appropriate according to the calcination temperature.

Furthermore, the orthophosphate of raw material may be crushed or miniaturized before calcination. Examples of a crushing equipment and a miniaturizing equipment are a ball mill, a rod mill, a hammer mill, an attrition mill, a micron mill, a colloid mill, a jet mill, the Single Track Jet Mill, a counter jet mill, a pindisk mill, the Jet-O-mizer and the Inomizer.

As a calcination equipment used for the producing method of the present invention, a heat kneading equipment, a warm air drying equipment and a calcination furnace can be used. Examples of them are an extruder, the Henschel mixer, a flash mixer, a paddle mixer, the Banbury mixer, a ribbon mixer, a crush mixer, a SC processor, the Plastomill, the KRC kneader, a vacuum kneader, a pressurization kneader, a calcination furnace, a batch calcination furnace, a pusher furnace, a mesh belt furnace, a fluid calcination furnace, a double shaft method continuation calcination furnace, a far infrared rays heating furnace, a far infrared rays conveyer furnace, a microwave calcination furnace, a crucible furnace, a hot air drying machine, a fluid bed dryer, a vibration dryer, a vibrating fluid bed dryer, a stirring dryer, a flash dryer, an aeration dryer, a shelf-type dryer, the Dry Meister, a drum dryer, an air dryer, a microwave dryer, a spray dryer, a disk dryer, a conical dryer, a paddle dryer, a hopper dryer, a rotary dryer, a rotary kiln, a roller hearth kiln, a tunnel kiln and a shuttle kiln.

In the producing method of the present invention, overreactions can be inhibited. Therefore, products made by overreaction, such as triphosphate and polyphosphate wherein dehydration condensation reaction was more progressed, are few. In addition, products, especially the sticky products made by the overreaction are scarcely attached to the inside wall of the calcination equipment. Therefore, the present invention is suitable for obtaining the high-purity pyrophosphate suitable as a flame retardant for synthetic resin.

Hereafter, the present invention will now be described in more detail referring to specific examples and comparative examples, but it should be understood that the present invention is not limited by these descriptions. The numerical values of purity of the melamine pyrophosphates obtained by the following examples 1 to 10 are obtained by the following analyzing method.

<Measuring Method for Purity>

The purity of melamine pyrophosphate was measured by using the HPLC equipment manufactured by Senshu Scientific Co., ltd. (Pump; SSC-3150, RI detector; ERC-7515A), the Column Oven manufactured by JASCO Corporation (CO-965) and the OH pak column manufactured by Shodex (SB-802.5 HQ).

EXAMPLE 1

A stainless steel vat containing the orthophosphoric acidmelamine was put into a hot air dryer, and was calcined by heating at 200° C.-260° C. and stirring sometimes to obtain the white powder of melamin pyrophosphate. The purity of melamine pyrophosphate obtained was 96.5%.

EXAMPLE 2.

The orthophosphoric acidmelamine was heated and stirred by using a kneader having an oil jacket, then was calcined at 200° C.-250° C. to obtain the white powder of melamine pyrophosphate. The purity of melamine pyrophosphate obtained was 98.2%.

EXAMPLE 3

The orthophosphoric acidmelamine was heated and stirred by means of the Henshel mixer (manufactured by Mitsui Mining Co., Ltd.(Changed to Nippon Coke & Engineering Co., Ltd. from 2009), FN150J/T) using the heat medium, and was calcined at 170° C.-250° C. to obtain the white powder of melamine pyrophosphate. The purity of melamine pyrophosphate obtained was 97.1%.

EXAMPLE 4

The orthophosphoric acidmelamine was heated and stirred by means of the fluid bed dryer (manufactured by Okawara Mfg. Co., Ltd.), and was calcined at 230° C.-260° C. to obtain the white powder of melamine pyrophosphate. The purity of melamine pyrophosphate obtained was 96.8%.

EXAMPLE 5

The orthophosphoric acidmelamine was heated and stirred by means of the rotary kiln (manufactured by Kurimoto, Ltd.), and was calcined at 200° C.-260° C. to obtain the white powder of melamine pyrophosphate. The purity of melamine pyrophosphate obtained was 97.5%.

EXAMPLE 6

The orthophosphoric acidmelamine was heated and stirred by means of the paddle dryer (manufactured by Nara Machinery Co., Ltd.), and was calcined at 200° C.-260° C. to obtain the white powder of melamine pyrophosphate. The purity of melamine pyrophosphate obtained was 97.3%.

EXAMPLE 7

The orthophosphoric acidmelamine was heated and stirred by means of the extruder (manufactured by The Japan Steel Works, LTD., TEX44αII-52.5BW), and was calcined at 200°

C.-260° C. to obtain the white powder of melamine pyrophosphate. The purity of melamine pyrophosphate obtained was 98.1%.

EXAMPLE 8

The orthophosphoric acidmelamine was heated and stirred by means of the vibration dryer (manufactured by Chuo Kakohki Co., Ltd.), and was calcined at 200° C.-260° C. to obtain the white powder of melamine pyrophosphate. The purity of melamine pyrophosphate obtained was 96.8%.

EXAMPLE 9

The orthophosphoric acidmelamine was heated by means of a far infrared rays conveyor furnace, and was calcined at 220° C.-230° C. to obtain the white powder of melamine pyrophosphate. The purity of melamine pyrophosphate obtained was 96.1%.

EXAMPLE 10

The orthophosphoric acidmelamine was put in a microwave calcination furnace and was calcined at 200° C.-280° C. by heating and stirring sometimes to obtain the white powder of melamine pyrophosphate. The purity of melamine pyrophosphate obtained was 97.5%.

COMPARATIVE EXAMPLE 1

A stainless steel bat containing the orthophosphoric acid-melamine was put into a hot air dryer and was calcined at 90° C.-100° C. by heating and stirring sometimes. However, the melamine pyrophosphate was not produced.

COMPARATIVE EXAMPLE 2

A stainless steel bat containing the orthophosphoric acid-melamine was put into a hot air dryer and was calcined at 380° C.-400° C. by heating and stirring sometimes to obtain the white powder. The obtained white powder was analyzed. The purity of melamine pyrophosphate was 65.1%, which was low, and it was found that triphosphate and also polyphosphate wherein a dehydration condensation reaction was further progressed were produced.

Industrial Applicability

According to the producing method of the present invention, products made by overreaction, such as triphosphate and polyphosphate wherein dehydration condensation reaction is more progressed, become few, since overreactions can be inhibited. In addition, products, especially the sticky products made by the overreaction are scarcely attached to the inside wall of the calcination equipment. Therefore the high-purity pyrophosphate suitable as a flame retardant for synthetic resin can be obtained easily. Thus, the present invention is remarkably useful and helpful in the field of industrial application.

The invention claimed is:

1. A method of producing a melamine pyrophosphate powder, comprising producing said powder by calcination of melamine orthophosphate at 120° C. -350° C., in solid phase, with stirring, whereby said melamine pyrophosphate powder has a purity of 96.5% or more.

2. The method according to claim 1, wherein the calcination temperature is 150° C. -300° C.

3. The method according to claim 2, wherein the calcination temperature is 160° C. -280° C.

4. The method according to claim 1, wherein the melamine orthophosphate has 1 mol of melamine bound with 1 mol of orthophosphoric acid.

5. The method according to claim 1, wherein heating and stifling is effectuated in heated kneading equipment, warm air drying equipment or a calcination furnace.

6. The method according to claim 1, wherein heating and stifling is effectuated in an extruder, a Henschel mixer, a flash mixer, a paddle mixer, a Banbury mixer, a ribbon mixer, a crush mixer, a SC processor, a vacuum kneader, a pressurization kneader, a calcination furnace, a batch calcination furnace, a pusher furnace, a mesh belt furnace, a fluid calcination furnace, a double shaft method continuation calcination furnace, a far infrared ray heating furnace, a far infrared ray conveyer furnace, a microwave calcination furnace, a crucible furnace, a hot air drying machine, a fluid bed dryer, a vibration dryer, a vibrating fluid bed dryer, a stifling dryer, a flash dryer, an aeration dryer, a shelf dryer, a drum dryer, an air dryer, a microwave dryer, a spray dryer, a disk dryer, a conical dryer, a paddle dryer, a hopper dryer, a rotary dryer, a rotary kiln, a roller hearth kiln, a tunnel kiln or a shuttle kiln.

7. The method according to claim 1, wherein heating and stifling is effectuated in a hot air dryer, a kneader having an oil jacket, a fluid bed dryer, a rotary kiln, a paddle dryer, an extruder, a vibration dryer, a far infrared ray furnace or a microwave calcination furnace.

8. The method according to claim 1, wherein heating and stifling are performed continuously during production of melamine pyrophosphate.

* * * * *